United States Patent
Mulhauser

(12) 
(10) Patent No.: US 6,208,896 B1
(45) Date of Patent: Mar. 27, 2001

(54) METHOD AND APPARATUS FOR PROVIDING VARIABLE DEFIBRILLATION WAVEFORMS USING SWITCH-MODE AMPLIFICATION

(75) Inventor: Daniel F. Mulhauser, Wyndham, NH (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/191,662

(22) Filed: Nov. 13, 1998

(51) Int. Cl.[7] .................................................. A61N 1/39
(52) U.S. Cl. ................................................................ 607/5
(58) Field of Search .................................. 607/5, 7, 4, 74

(56) References Cited

U.S. PATENT DOCUMENTS

| | | | |
|---|---|---|---|
| 4,056,105 | 11/1977 | Ravas | 128/419 |
| 4,328,808 | 5/1982 | Charbonnier et al. | 128/419 |
| 4,499,907 | 2/1985 | Kallok et al. | 128/786 |
| 4,800,883 | 1/1989 | Winstrom | 128/419 |
| 4,823,796 | 4/1989 | Benson | 128/419 |
| 4,840,177 | 6/1989 | Charbonnier et al. | 128/419 |
| 4,989,603 | 2/1991 | Carroll et al. | 128/419 |
| 4,993,423 | 2/1991 | Stice | 128/696 |
| 5,020,541 | 6/1991 | Marriott | 128/723 |
| 5,025,172 | 6/1991 | Carroll et al. | 307/261 |
| 5,083,562 | 1/1992 | de Coriolis et al. | 128/419 |

(List continued on next page.)

FOREIGN PATENT DOCUMENTS

WO 95/05215  2/1885  (WO) .

OTHER PUBLICATIONS

Richard C. Dorf, "The Electrical Engineering Handbook", 1993, pp. 708–711.

"Comparison of Monophasic and Biphasic Defibrillating Pulse Waveforms for Transthoracic" Green et al., Reprinted from The Jun. 1 Issue The American Journal of Cardiology, Copyright 1995, pp. 1135–1139.

(List continued on next page.)

*Primary Examiner*—Kennedy Schaetzle

(57) ABSTRACT

A method and apparatus for providing variable defibrillation waveforms using switch-mode amplification are provided. In one embodiment, a defibrillation waveform generator is described that includes a rapid-discharge capacitor, a controller, and a switch-mode amplifier. The rapid-discharge capacitor is charged to a charge voltage that may be discharged over a time frame consistent with the chronaxie time of a human heart. The controller generates at least one control signal, which may be pulse-width modulated. The switch-mode amplifier responsive to the control signals, optionally supplemented by a biphasic converter, selectively amplifies the charge voltage so that the magnitude, phase, and timing of the amplification may be varied, thus resulting in a variable waveform. In some embodiments, the present invention includes both step-up and step-down converters. The step-down converter enables the defibrillator to be used so that the rapid-discharge energy storage device is charged to a charge voltage that is greater than the output voltage applied to the defibrillation patient. The step-up converter is used to maintain or increase the output voltage as the charge voltage is depleted. The step-up and step-down converters of the switch-mode amplifier may be employed in either order, i.e., step-down followed by step-up, or step-up followed by step-down. A step-down followed by step-up topology may permit the use of fewer components, or fewer of certain types of components. A step-up followed by step-down topology provides a constant-current source that may produce a particularly efficacious electrotherapeutic effect.

32 Claims, 6 Drawing Sheets

U.S. PATENT DOCUMENTS

| | | | |
|---|---|---|---|
| 5,111,813 | 5/1992 | Charbonnier et al. | 128/419 |
| 5,222,480 | 6/1993 | Couche et al. | 128/419 |
| 5,222,492 | 6/1993 | Morgan et al. | 128/419 |
| 5,224,486 | 7/1993 | Lerman et al. | 128/696 |
| 5,225,769 | 7/1993 | Fincke et al. | 324/127 |
| 5,230,336 | 7/1993 | Fain et al. | 607/7 |
| 5,247,939 | 9/1993 | Sioquist et al. | 128/697 |
| 5,265,588 | 11/1993 | Nelson et al. | 607/5 |
| 5,275,157 | 1/1994 | Morgan et al. | 607/6 |
| 5,334,219 | 8/1994 | Kroll | 607/5 |
| 5,352,239 | 10/1994 | Pless | 607/5 |
| 5,384,544 | 1/1995 | Flugstad et al. | 324/678 |
| 5,391,186 | 2/1995 | Kroll et al. | 607/5 |
| 5,411,526 | 5/1995 | Kroll et al. | 607/5 |
| 5,431,686 | 7/1995 | Kroll et al. | 607/7 |
| 5,447,522 | 9/1995 | Chang et al. | 607/7 |
| 5,488,553 | 1/1996 | Renger | 363/21 |
| 5,496,349 | 3/1996 | Campbell et al. | 607/5 |
| 5,514,160 | 5/1996 | Kroll et al. | 607/5 |
| 5,522,853 | 6/1996 | Kroll | 607/5 |
| 5,531,764 | 7/1996 | Adams et al. | 607/5 |
| 5,531,765 | 7/1996 | Pless | 607/5 |
| 5,591,209 | 1/1997 | Kroll | 607/5 |
| 5,593,427 | 1/1997 | Gliner et al. | 607/7 |
| 5,601,610 | 2/1997 | Persson | 607/5 |
| 5,601,612 | 2/1997 | Gliner et al. | 607/7 |
| 5,607,454 | 3/1997 | Cameron et al. | 607/5 |
| 5,620,465 | 4/1997 | Olson et al. | 607/5 |
| 5,620,470 | 4/1997 | Gliner et al. | 607/7 |
| 5,643,323 | 7/1997 | Kroll et al. | 607/2 |
| 5,645,573 | 7/1997 | Kroll et al. | 607/7 |
| 5,658,319 * | 8/1997 | Kroll | 607/7 |
| 5,722,995 | 3/1998 | Olson et al. | 607/5 |
| 5,725,560 | 3/1998 | Brink | 607/5 |
| 5,728,139 | 3/1998 | Post | 607/6 |
| 5,733,310 | 3/1998 | Lopin et al. | 607/7 |
| 5,735,878 | 4/1998 | Kroll et al. | 607/5 |
| 5,745,350 | 4/1998 | Archer et al. | 363/15 |
| 5,749,905 | 5/1998 | Gliner et al. | 607/7 |
| 5,769,872 | 6/1998 | Lopin et al. | 607/5 |
| 5,782,880 | 7/1998 | Lahtinen et al. | 607/9 |
| 5,792,189 | 8/1998 | Gray et al. | 607/5 |
| 5,803,927 | 9/1998 | Cameron et al. | 607/5 |

OTHER PUBLICATIONS

"Truncated Biphasic Pulses for Transthoracic Defibrillation" Bardy et al., Circulation vol. 91, No. 6, Mar. 15, 1995, pp. 1768–1774.

"Multicenter Comparison of Truncated Biphasic Shocks and Standard Damped Sine Wave Monophasic Shocks for Transthoracic Ventricular Defibrillation", Bardy et al, Circulation, vol. 94, No. 10, Nov. 15, 1996, pp. 2507–2514.

"Defibrillation of 100 kg calves with asymmetrical, bidirection, rectangular pulses", Schuder et al., Cardiovascular Research, 1984, vol. 18, pp. 419, 421, 423 and 425.

"Biphasic waveforms—not yet proven in "real world" patients", by Fred Chapman, PhD, research Physio–Control, Annual Int'l Conference of the IEEE Engineering in Medicine and Biology, Society, vol. No. 2, 1991.

"Ventricular Defibrillation Using Biphasic Waveforms: The Importance of Phasic Duration", Tang et al., JACC vol. 13, No. 1, Jan. 1989; pp. 207–214.

"Large Change in Voltage at Phase Reversal Improves Biphasic Defibrillation Thresholds, Parallel–Series Mode Switching" Yamanouchi et al., Circulation, vol. 94, No. 7, Oct. 1, 1996, pp. 1768–1773.

* cited by examiner

METHOD AND APPARATUS FOR PROVIDING VARIABLE DEFIBRILLATION WAVEFORMS USING SWITCH-MODE AMPLIFICATION

BACKGROUND OF THE INVENTION

1. Field of the Invention

The present invention relates generally to a defibrillator and, more particularly, to a defibrillator that provides variable waveforms.

2. Related Art

A defibrillator is a device used to administer a high intensity electrical shock through two or more electrodes, commonly referred to as "paddles" or "pads," to the chest of a patient in cardiac arrest. A selected, discrete quantity of energy is typically stored in a charge-storage device (e.g., a capacitor) and is then electrically discharged into the patient through the paddle circuit.

Defibrillation is not a procedure with a certain and successful outcome. Rather, the probability of successful defibrillation depends on the condition of the patient and on various defibrillation discharge parameters, such as the intensity and shape of the defibrillation waveform. The term "intensity" as used herein refers to the level of the electrical discharge, which may be measured by the energy stored in the defibrillator, energy delivered to the patient, peak or average current flowing through the patient, electrical charge or integrated electron flow through the patient, and various other measures.

In order to practice defibrillation successfully and safely, it is important that the defibrillator be capable of providing an electrical discharge having an optimal combination of discharge parameters. For example, if the selected discharge intensity level is too low, defibrillation will not be successful and must be repeated at a higher intensity level until the patient is defibrillated. However, repeated defibrillation discharges at increasing intensity levels are more likely to cause damage to the heart. Also, repeated discharges cause the patient to remain in ventricular fibrillation for a longer time. This delay may cause the patient's condition to deteriorate, as metabolic imbalance and hypoxia develop, which, in turn, make the patient harder to defibrillate and reduce the prospect of successful recovery.

Moreover, optimal intensity generally varies in accordance with the pulse duration. That is, desirable values of peak or average current delivered to the patient, charge or energy delivered to the patient, or other measures of intensity, vary with pulse duration. More specific information in this regard is provided in U.S. Pat. No. 5,111,813 to Charbonnier, et al.

More generally, the shape of the pulse may influence the outcome of the defibrillation attempt. The word "shape" as used broadly includes such parameters as amplitude, duration, polarity, number of pulse phases, or form (such as rectilinear, sinusoidal, etc.). As applied here to the electrotherapeutic discharges generated by defibrillation devices, the word "shape" is synonymous with the word "waveform."

A wide variety of defibrillation waveforms are known. Some defibrillators employ monophasic (single polarity) current or voltage pulses. Others employ biphasic (both positive and negative polarity) pulses. Either monophasic or biphasic pulses may have a variety of forms, such as sinusoidal, damped-sinusoidal, exponential, truncated-exponential, rectilinear, square, constant "tilt" (a measure of the difference between the start and end voltage, often expressed as the difference between the initial and final voltages, divided by the initial voltage), combinations of such forms, and so on. Moreover, the choice of which waveform to employ may depend not only on the condition or electrical characteristics of the patient, but also on whether the defibrillator is implanted in the patient or is applied externally to the patient. If the defibrillator is implanted, the patient's unique electrical characteristics and overall physiology may be investigated and the waveform tailored to that particular patient's needs. External defibrillators, in contrast, are intended to be applied to numbers of patients that have generally varying physiological characteristics. Moreover, the same patient may require different waveforms for optimal operation depending, for example, on the contact that is achieved between the paddles and the patient. Thus, external defibrillators may be designed for optimal use on an average patient. Alternatively, they may be designed so that they are capable of providing a variety of waveforms depending on an evaluation of the patient's physiology, the electrical connection achieved between the paddles and the patient, new knowledge about the operation and affect of electrotherapeutic discharges, or other factors.

In addition, the electrical requirements of defibrillators, particularly external ones, impose certain constraints on the type of circuitry, and components, that may practicably be used. In general, because of the indirect nature of the electrical connection (i.e., through skin and other tissue), external defibrillators operate at higher voltages and/or currents than implanted defibrillators. Thus, for example, the sizes of capacitors used as charge-storage devices typically are greater for external defibrillators as compared to internal ones, and often are more expensive. Also, other electronic components, such as solid state switches, diodes, inductors, resistors, and so on, must be capable of reliably operating in the relatively higher ranges of voltage and/or current. Moreover, because external defibrillators often are portable (because time is of the essence in applying the electrotherapeutic discharge), the weight of the device may also be an important factor. The weight of the defibrillator generally increases as the "size" of electrical components (i.e., their ability to generate, and operate under, higher voltages and/or currents) increases.

Therefore, it may be desirable that a defibrillator be capable of generating a variety of waveforms for electrotherapy (although such flexibility may not be important if, for example, a particular waveform is thought to be generally optimal). Moreover, it generally is desirable that the defibrillator employ components that are capable of operating at high voltages and/or currents, are not expensive, and are not heavy. Also, it is important that the defibrillator be capable of providing a complete electrotherapeutic discharge after only one charging of the charge storage device. If a second charging is required to complete the electrotherapy, potentially injurious delay results, the initial discharge may not have the intended therapeutic effect, and the repeated applications may injure the patient. Also, in an external defibrillator, the electrical characteristics of the paddle-patient connection may vary between applications.

Various defibrillation circuits are known that attempt to address one or more of these problems. For example, U.S. Pat. No. 5,749,905 to Gliner, et al., seeks to automatically vary an externally applied, biphasic, waveform by varying the duration of particular phases of the waveform depending on the electrical characteristics of the patient. This waveform manipulation is said to allow the production of a smaller, more efficient, and less expensive defibrillator. U.S. Pat. No. 5,769,872 to Lopin, et al., is directed to a defibrillation circuit that controls resistance between the charge-storage device and the paddles in order to manipulate a current waveform. A device is described in U.S. Pat. No. 5,222,492 to Morgan, et al., that uses pulse-width modulation to control the magnitude of a current administered to a patient.

Significantly, however, these and other known circuit designs do not optimally balance the need for variable waveforms with the need for smaller, lighter, and less expensive circuit components. For example, the capability of varying the waveform may be achieved in these devices by providing a high initial charge at the charge-storage device. As the waveform is generated, the initial charge dissipates and, in these known defibrillators, the amplitude of voltages (or currents) available to shape the waveform also generally declines. Pulses of longer duration, and/or higher amplitude during particular phases, thus may be achieved, but at the cost of providing a higher initial charge. As noted, this higher initial charge increases the weight and expense of the charge-storage device, and imposes greater voltage and/or current stresses on other electronic components in the defibrillation circuit.

Therefore, what is needed is a defibrillation device and method that enable a variable defibrillation waveform to be applied to a patient while reducing the voltage and/or current stresses on components.

SUMMARY OF THE INVENTION

In one embodiment, the present invention is a defibrillation waveform generator including a rapid-discharge energy storage device (typically, a capacitor), a controller, and an amplifier. The rapid-discharge capacitor is charged to a charge voltage that may be discharged over a time period consistent with the chronaxie time of a human heart. That is, the discharge capability is such that a voltage or current waveform may be generated that delivers energy over a time period suitable for defibrillation of a human heart. This time period, which may include a number of phases, is not necessarily the same as the chronaxie time, but is consistent with it so that a defibrillation waveform having appropriate overall duration, and appropriate durations of separate phases, may be administered. As noted above, the efficacy and safety of the defibrillation attempt are enhanced by selecting pulses or other waveforms of appropriate duration and intensity. For convenience, a rapid-discharge capacitor, or other energy storage device, with the capability to provide pulses or waveforms of such appropriate durations is said to be "tuned consistently with" the chronaxie time of a human heart. (More detailed information regarding the chronaxie time, and its relation to charge or current and pulse duration, is provided in U.S. Pat. No. 5,431,686 to Kroll, et al.)

The controller generates at least one control signal. The amplifier, responsive to the control signals, selectively amplifies the charge voltage. The word "selectively" is used in this context to mean that the control signals may be chosen so that the magnitude, phase, and/or timing of the amplification may be varied, thus resulting in a variable waveform.

Selective switch-mode amplification, as described herein, is advantageous because it conserves, rather than purposefully dissipates, energy in order to shape the waveforms. (Of course, nominal dissipation of energy occurs in the amplifier's components.) In contrast, known techniques typically employ waveform-generating techniques that dissipate energy. For example, the waveform-generating circuit described in U.S. Pat. No. 5,769,872 to Lopin, et al., varies resistance to control the discharge of the charge-storage device. Energy thus is generally dissipated to achieve a desired waveform. Notwithstanding the therapeutic benefits of achieving a desired waveform, there are costs in the size and expense of components, noted above, to such known techniques. In contrast, with respect to the present invention, conservation of energy provides significant advantages for the design and operation of a defibrillator. The maximum voltages and/or currents to which circuit components are exposed may generally be reduced as compared to devices in which energy is dissipated. Thus, as noted, smaller and less expensive components may be employed in the present invention, and the likelihood of their failure due to the stresses of high voltage and/or current is reduced.

In some embodiments, the amplifier is a switch-mode amplifier. Switch-mode amplification is a particularly advantageous technique in this context because the switch components, typically semiconductors, are fully on or fully off rather than in a linear region. Typically, semiconductors dissipate more energy when operated in their linear regions than when in a fully on or off state. The switch-mode amplifier, as other amplifier implementations, is responsive to one or more control signals generated by the controller. In some embodiments, at least one control signal is pulse-width modulated or pulse-frequency modulated. In various implementations of these embodiments, pulse-width or pulse-frequency modulation may be accomplished by various techniques such as fixed-frequency, variable pulse-width, constant-pulse-width, variable-frequency (including constant-on-time or constant-off-time), hysteretic, or others.

In some embodiments, the amplifier includes a step-up converter that has at least one boost switch. This boost switch is responsive to a first control signal generated by the controller. (The term "boost switch" is used to refer to a switch, typically a semiconductor, used to enable a step-up converter to be operated in a switch mode.) The step-up converter thus selectively amplifies the charge voltage of the rapid-discharge energy storage device to generate an amplified voltage. In some implementations of this embodiment, the amplifier also includes an output energy storage device having an output voltage, constructed and arranged to provide a filter. The output energy storage device additionally may shunt leakage or other undesirable currents away from the patient. In other implementations, the amplifier further includes a step-down converter. The step-down converter has at least one buck switch responsive to a second control signal from the controller. (The term "buck switch" is used to refer to a switch, typically a semiconductor, used to enable a step-down converter to be operated in a switch mode.) In one aspect, the step-down converter selectively decreases the charge voltage. In another aspect, the step-down converter selectively decreases the amplified voltage generated by the step-up converter. In some embodiments, the boost switch and the buck switch may be the same switch; i.e., only one switch need be employed in those embodiments even though both step-up and step-down conversions are implemented.

In another embodiment, the invention is a defibrillation waveform generator in which the amplifier includes a step-down converter that selectively decreases the charge voltage of the rapid-discharge energy storage device. The step-down converter includes at least one buck switch that is responsive to a control signal from a controller. The step-down converter generates an output that is referred to for convenience as the "step-down voltage." The amplifier also includes a step-up converter that selectively amplifies the output of the step-down converter to generate an amplified voltage. The step-up converter has at least one boost switch responsive to a control signal from the controller. In some implementations of this embodiment, the amplifier also includes an output energy storage device that filters energy provided by the step-up converter. In some implementations, the step-down converter and the step-up converter share an inductor and/or a capacitor. In some implementations, the buck switch and the boost switch are the same switch.

The step-up converter provides the advantage noted above with respect to the use of amplification to conserve energy. Thus, the amplifier of the present invention includes a step-up converter, but need not include a step-down converter. Unlike known devices and techniques, the amplifier of the present invention does not utilize a step-down converter alone, i.e., without a step-up converter. (For a description of a device having step-down conversion but not step-up conversion, see U.S. Pat. No. 5,222,492 to Morgan, et al.) Use of a step-up converter enhances the ability to provide a constant current waveform to the patient, which is thought to be beneficial (see, e.g., U.S. Pat. No. 4,840,177 to Charbonnier, et al.). More specifically, the step-up converter enables the more efficient generation (i.e., by conserving energy using typically smaller and lighter components) of a constant voltage for a constant-impedance patient, or a voltage waveform that changes to retain constant current as patient impedance changes.

Some embodiments of the present invention advantageously include both step-up and step-down converters. The step-down converter enables the defibrillator to be used so that the rapid-discharge energy storage device is charged to a charge voltage that is greater than the output voltage (the output voltage is the voltage applied to the patient, optionally including biphasic conversion and typically, but not necessarily, gated by a patient isolation relay, as described below). The additional energy thus provided to the defibrillation waveform generator may be used by either or both of the step-down and step-up converters to optimize the range of variation of the duration of the waveform. For example, in a biphasic, rectilinear waveform, a first positive pulse and/or a second negative pulse may be extended in time while conserving energy. As noted below, a biphasic converter may also be employed. A defibrillation waveform may be more efficacious if it includes a phase reversal having a large rate of change of voltage. Because the step-up converter maintains, or increases, the output voltage, and thus allows large swings of voltage using a biphasic converter, the present invention is particularly well suited for providing this effect.

Also, as will be apparent from the detailed description of illustrative embodiments below, topologies including both step-up and step-down converters generally result in greater efficiencies than typically are achieved using either type of converter alone. In addition, as noted, the voltage and/or current extremes presented to the components generally are less. Thus, components are generally subjected to lower voltage and current stresses both in terms of absolute values and ranges of values. This reduced operational stress allows designs that increase reliability, reduce expense, reduce weight, or provide a combination of these advantages. The inclusion of a step-down converter has the additional advantage of providing short-circuit protection, because the path from the energy storage device to the patient may be interrupted or broken. In contrast, in a simple, non-isolated, step-up converter (i.e., one without a transformer), the path from the energy storage device to the patient generally cannot be broken.

There is yet a further advantage to the inclusion of a step-down converter together with a step-up converter in topologies in which the output energy storage device (which holds the output voltage applied to the patient directly or through a biphasic converter and/or patient isolation relay) is not charged at the same time as the rapid-discharge energy storage device. Rather, the output energy storage device is charged, in accordance with these topologies, at the time of discharge of the output voltage into the patient. In embodiments employing these topologies, the step-down converter allows a ramp-up of the output voltage so that leakage to the applied patient circuit is shunted away from that circuit.

Also advantageously, the step-up and step-down converters of the switch-mode amplifier may be employed in either order, ie., step-down followed by step-up, or step-up followed by step-down. As will be described below, a step-down then step-up topology may permit fewer components, or fewer of certain types of components, to be used. However, a step-up followed by step-down topology also has an advantage in that the output current may be provided by an inductor rather than a capacitor. This arrangement typically results in an amplifier that is a better constant-current source than the alternative topology. A yet further advantage of the step-up followed by step-down topology is that the output inductor, and the impedance of the patient's body, may be used to provide an appropriate output time constant for filtering the switched output waveform without the use of an output capacitor.

In one embodiment, the defibrillation waveform generator also includes a feedback sensor. The feedback sensor senses an "indicator of patient impedance." This term is used to refer to a measure that is indicative of the impedance of the patient's body, including the impedance presented by the connection of the defibrillator to the patient (i.e., the connections between the paddles and the patient's body), in combination with the output of the amplifier. This measure typically is a measure of voltage, current, or both. Techniques for calculating patient impedance by such measures are well known to those skilled in the relevant art. In some implementations, a voltage or current provided by the step-up converter is sensed by the feedback sensor. In other implementations, a voltage or current provided by the step-down converter, or by the output energy storage device, may be sensed. In all of these implementations, the sensed voltage and/or current is provided to the controller of the defibrillation waveform generator.

The advantages of sensing the patient's impedance, and using this feedback informing to adjust the defibrillation waveform accordingly, are well known. See, for example, the use of impedance-normalized delivered energy to improve the probability of successful defibrillation while reducing the risk of damage to the myocardium and nerve system of the heart, described in U.S. Pat. No. 5,111,813 to Charbonnier, et al. In accordance with illustrated embodiments of the present invention, the controller controls the switching of the boost and/or buck switches in accordance with sensed feedback voltage(s) or feedback current(s). This feedback information is indicative of the patient's impedance and the charge or energy being delivered to the patient.

The defibrillation waveform generator may also include a biphasic converter, such as an H-bridge. As noted, a biphasic defibrillator waveform may have desirable thereapeutic properties. In alternative implementations, the biphasic converter may convert the output of the output energy storage device, the step-up converter, or the step-down converter. In any of these implementations, the biphasic waveform that is the output of the biphasic converter is referred to for convenience as the "biphasic output voltage." It will be understood that in this context, as with respect to other references to voltage or voltage waveforms, equivalent references could be made with respect to current, or current waveforms. For example, reference could equivalently be made to a biphasic output current, or biphasic output current waveform.

The defibrillation waveform generator may also include a patient isolation relay that selectively isolates the output voltage, or the biphasic output voltage, from the patient. As is well known to those skilled in the relevant art, the purpose of the patient isolation relay is to prevent premature exposure of the patient (or exposure of the operator) to voltages or currents that might occur through normal leakage of components, such as semiconductor switches; as a result of component failure; or for other reasons.

In some embodiments, the defibrillation waveform generator also includes a waveform definer that provides to the controller at least one parameter of at least one defibrillation waveform. For example, the waveform definer may specify to the controller that the waveform is to consist of a positive, rectilinear pulse followed by a negative, rectilinear pulse, and further specify the durations of each pulse and of the total waveform.

The defibrillation waveform generator may further include an initial impedance sensor that provides to the controller an initial indicator of patient impedance, or other parameter descriptive of the patient's electrical characteristics. Alternatively, this initial indicator may be provided to the waveform definer. In either case, the purpose is to enable the controller to tailor the waveform and the initial energy stored (the charge voltage) so that the electrotherapeutic discharge is appropriate to the impedance of the patient.

In another embodiment, the present invention is a defibrillator including a power supply, a defibrillation voltage generator electrically coupled to the power supply, and a defibrillation waveform generator. The defibrillation voltage generator generates a defibrillation voltage that is provided to the rapid-discharge energy storage device. The defibrillation waveform generator includes a rapid-discharge energy storage device, a controller, and an amplifier, such as a switch-mode amplifier, responsive to control signals generated by the controller. In one embodiment, the amplifier includes a step-up converter, and in other embodiments includes both step-down and step-up converters. The defibrillation waveform generator may be implanted in, or, alternatively, externally coupled to, a human being. That is, the defibrillator may be an external, or an internal, defibrillator.

In another embodiment, the invention is a defibrillation waveform-generation circuit for generating a defibrillator waveform. The circuit includes a rapid-discharge capacitor tuned to a chronaxie time of a human heart, having a source node electrically coupled to a charge voltage and a common node electrically coupled to a common voltage (such as ground). The circuit also includes a controller that generates at least one control signal, and a step-up converter. The control signal may be pulse-width or pulse-frequency modulated. The step-up converter includes an inductor having an input node electrically coupled to the source node and having an output node; a boost switch having a control node responsive to a first control signal, a common node coupled to the common voltage, and a first node electrically coupled to the output node of the inductor; a boost diode having an input node electrically coupled to the first node of the boost switch and having an output node; and an output capacitor having a common node electrically coupled to the common voltage and an output node electrically coupled to the output node of the boost diode. The boost switch and/or boost diode may be an insulated-gate bipolar transistor, a power field-effect transistor, or any other known solid state device or similar device now developed or to be developed in the future. The boost diode may also be properly synchronized transistor switches.

The circuit may also include a step-down converter. The step-down converter includes a buck switch having a control node responsive to a second control signal, a first node coupled to the source node, and a second node electrically coupled to the input node of the inductor. The step-down converter also includes a buck diode having an input node electrically coupled to the common voltage and an output node electrically coupled to the second node of the buck switch. The buck switch may be an insulated-gate bipolar transistor, a field-effect transistor, or any of a variety of other known switch devices now known or to be developed in the future. The buck diode may be any of a variety of known diodes, an insulated-gate bipolar transistor, a field-effect transistor, or any of a variety of other known devices now known or to be developed in the future.

In a further embodiment, the invention is a method for generating a defibrillator waveform. The method includes charging a rapid-discharge energy storage device to a charge voltage, wherein the storage device is tuned to a chronaxie time of a human heart; generating at least one control signal; and selectively amplifying the charge voltage responsive to one or more of the control signals. The generating step may include generating a pulse-width modulated, or pulse-frequency modulated, control signal. The selectively amplifying step may include switch-mode amplifying. The selectively amplifying step may include step-up converting for selectively maintaining the charge voltage. The selectively amplifying step may further include step-down converting for selectively decreasing the charge voltage, wherein the step up converting is responsive to a first control signal and the step-down converting is responsive to a second control signal.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps in which the leftmost digit of a reference numeral indicates the number of the figure in which the referenced element or step first appears (for example, the element 210 appears first in FIG. 2), and wherein.

DETAILED DESCRIPTION

The attributes of the present invention and its underlying method and architecture will now be described in greater detail with reference to one embodiment of the invention, referred to as defibrillator 105. Defibrillator 105 is described in particular with reference to an illustrative embodiment of one of its elements, defibrillation waveform generator 100.

Figure 1:
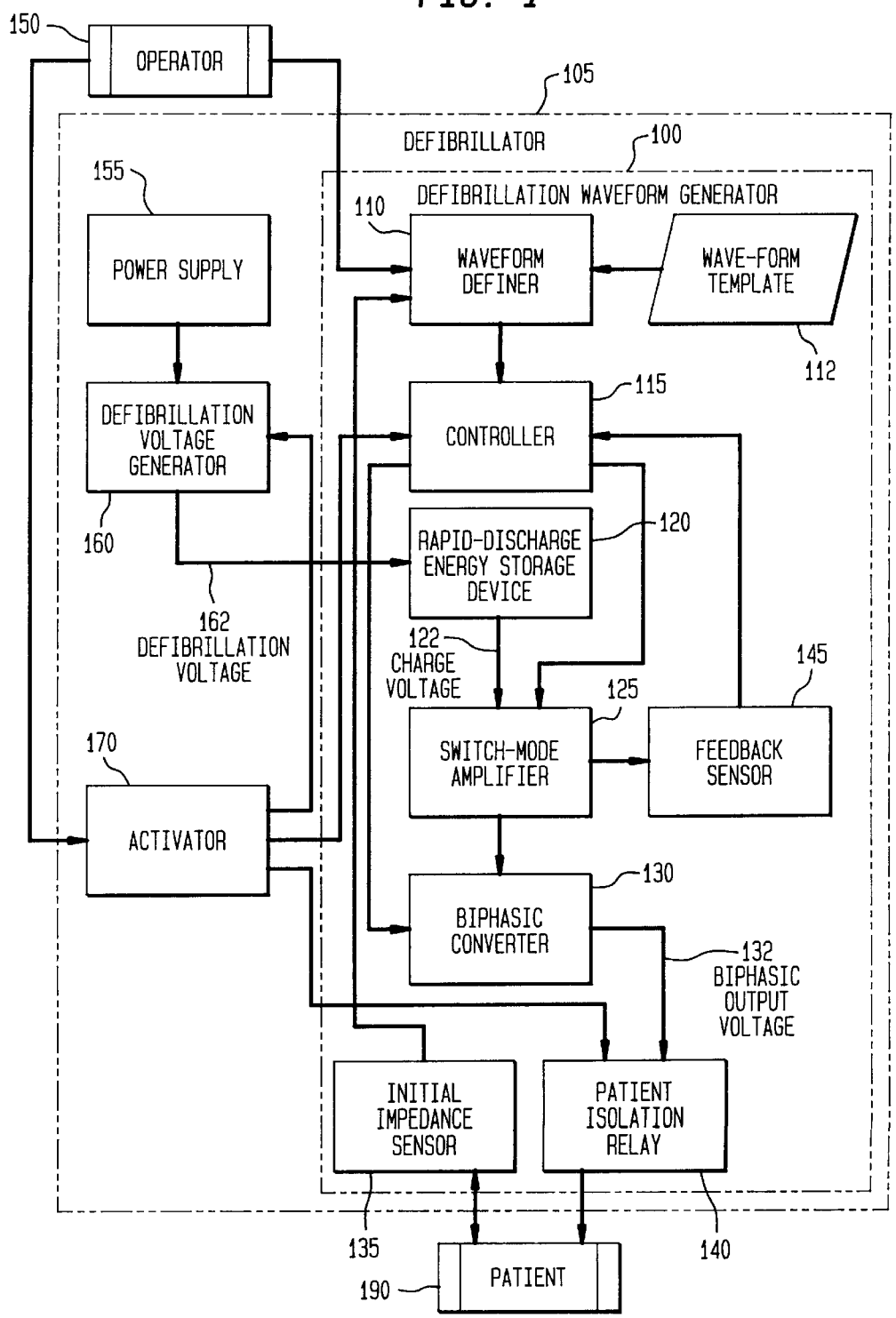
FIG. 1 is a functional block diagram of one embodiment of a defibrillator, including a defibrillation waveform generator, in accordance with the present invention.

FIG. 1 is a functional block diagram of defibrillator 105. As shown in FIG. 1, defibrillator 105 includes power supply 155, defibrillation voltage generator 160, and activator 170, all of which are known elements of a defibrillator. In accordance with the present invention defibrillator 105 also includes defibrillation waveform generator 100.

POWER SUPPLY 155, DEFIBRILLATION VOLTAGE GENERATOR 160, AND ACTIVATOR 170

Power supply 155 may be any of a variety of known power supplies appropriate for use with external or internal defibrillators. Power supply 155 provides a voltage that is processed in accordance with known techniques by defibrillation voltage generator 160 to generate defibrillation voltage 162. Defibrillation voltage 162 is provided to rapid-discharge energy storage device 120 to charge it to a charge voltage 122 that is of an appropriate intensity for generating a defibrillation waveform.

Defibrillation voltage generator 160 is activated by activator 170. Because of the high energy levels generated by generator 160, and the dangers to patients or operators due to an accidental discharge of defibrillator 105, generator 160 typically remains in an deactivated state until its use is required to defibrillate a patient. Activator 170 is, in turn, enabled by operator 150. In an external defibrillator, operator 150 typically is a human being, but it may be a machine. In an internal defibrillator, operator 150 typically is a device that detects ventricular fibrillation, or other abnormal heart activity that may be susceptible to electrotherapy, and automatically activates the internal defibrillator by enabling activator 170. Activator 170 may be any of a variety of known devices, typically including known switches, relays, logic circuits and elements, and/or other elements. As noted below, activator 170 also activates controller 115 and optional patient isolation relay 140.

DEFIBRILLATION WAVEFORM GENERATOR 100

Defibrillation waveform generator 100 generates a variable defibrillation waveform. Generator 100 includes rapid-discharge energy storage device 120, switch-mode amplifier 125, and controller 115. Generator 100 also optionally includes biphasic converter 130, patient isolation relay 140, initial impedance sensor 135, and waveform definer 110. It will be understood that defibrillation waveform generator 100 is illustrative only, and that many alternative implementations may be used in accordance with the present invention.

Rapid-Discharge Energy Storage Device 120

As noted, rapid-discharge energy storage device 120 stores energy provided to it from defibrillation voltage generator 160 to build up a charge voltage 122. Typically device 120 is any of a variety of known energy storage devices for use in a defibrillator, such as a film capacitor having a capacitance in the range of approximately 100 to 200 microfarads and capable of holding a charge voltage on the order of thousands of volts. In one of many other illustrative examples of known defibrillator rapid-discharge energy storage devices, device 120 may include a number of aluminum electrolytic photo flash capacitors arranged in series. It is not material to the present invention which of many known devices, or others to be developed in the future, are used, provided that device 120 is capable of storing, and rapidly discharging, a charge appropriate for defibrillation.

Switch-Mode Amplifier 125

Figure 2:
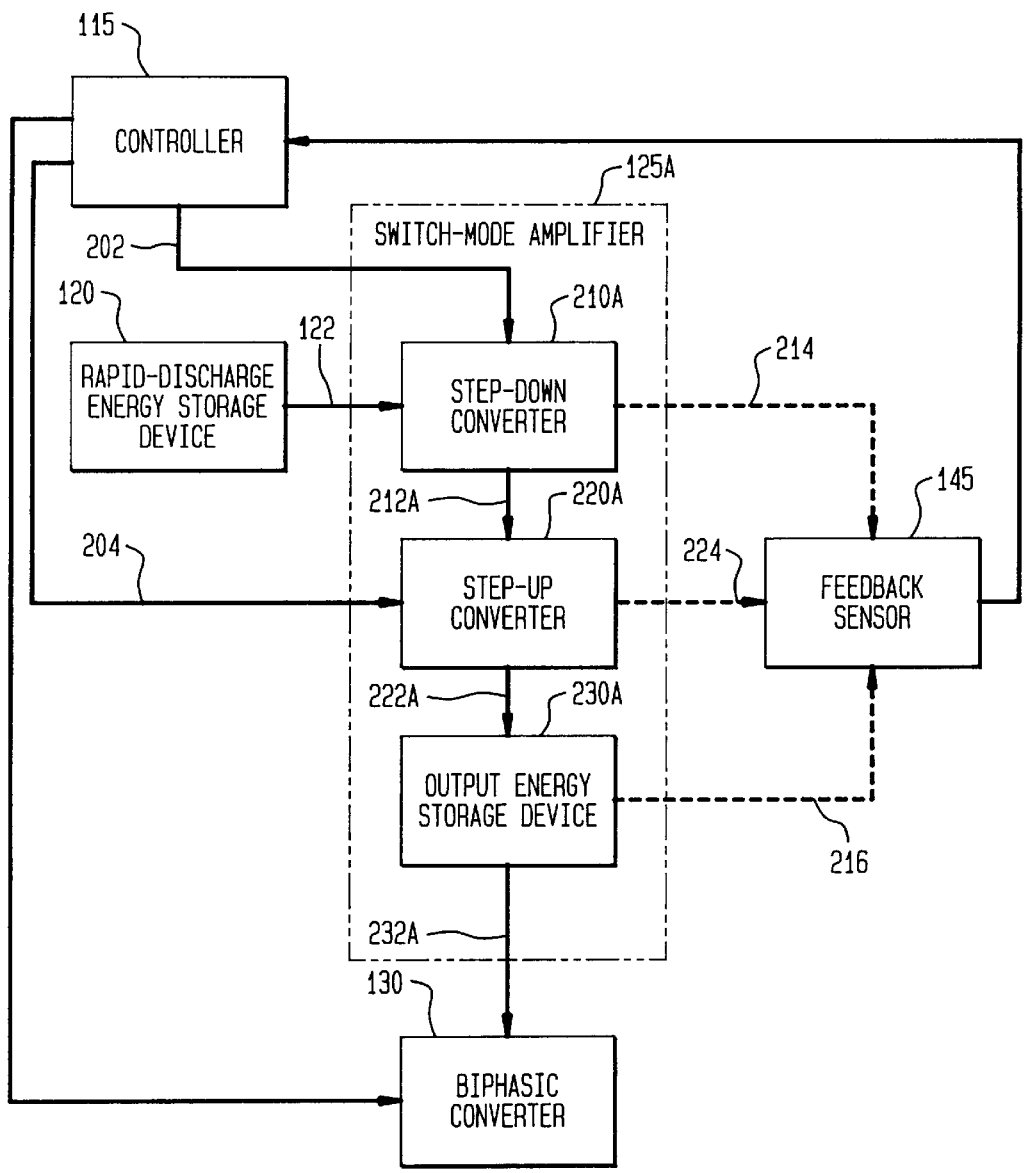
FIG. 2 is a functional block diagram of one embodiment of a switch-mode amplifier of the defibrillation waveform generator of FIG. 1.
Figure 3:
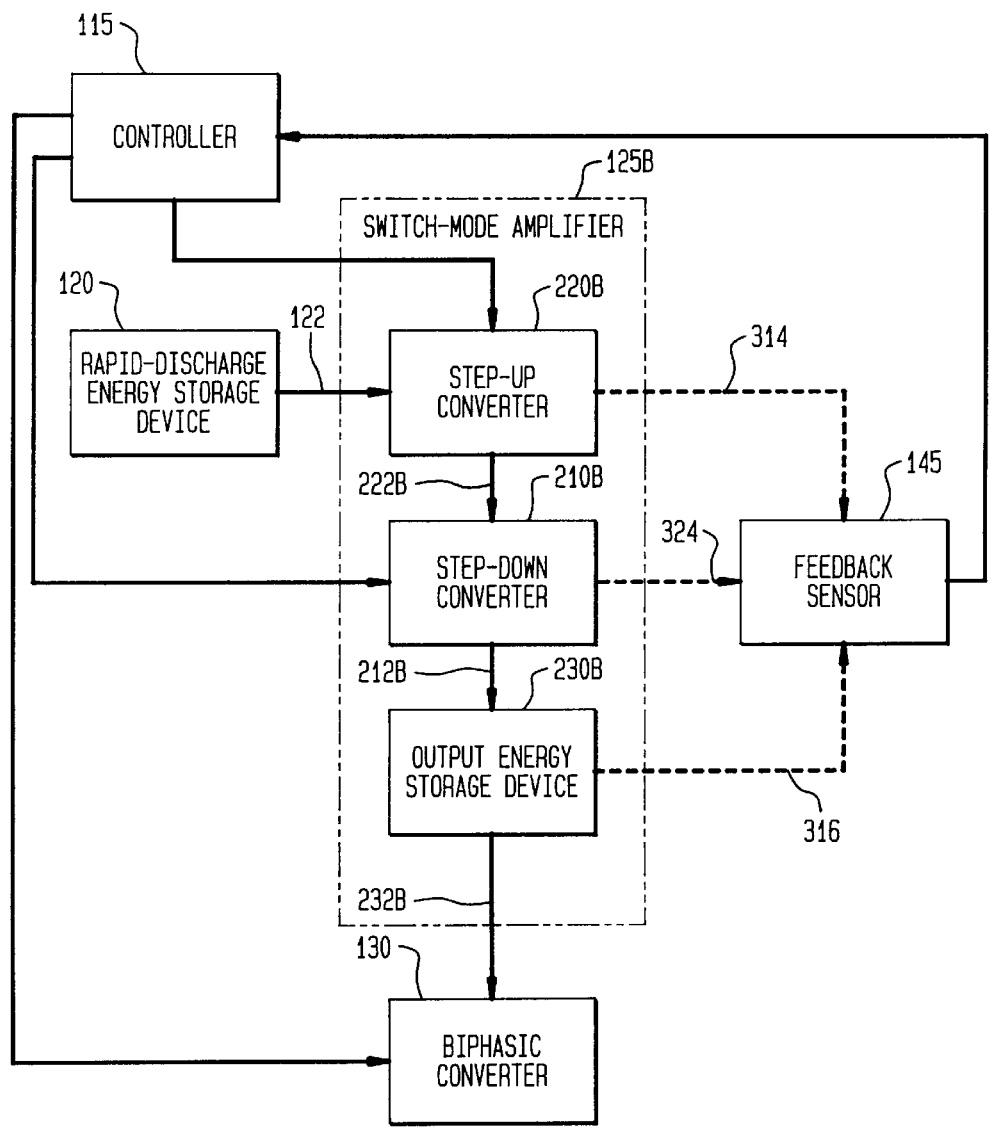
FIG. 3 is a functional block diagram of another embodiment of a switch-mode amplifier of the defibrillation waveform generator of FIG. 1.

FIG. 2 is a functional block diagram of one embodiment of switch-mode amplifier 125, referred to as switch-mode amplifier 125A. Switch-mode amplifier 125A is illustrative only; many alternative embodiments are possible in accordance with the invention. For example, FIG. 3 is a functional block diagram of an alternative embodiment referred to as switch-mode amplifier 125B. Amplifiers 125A and 125B both include step-up converter 220, step-down converter 210, and output energy storage device 230. However, the connections among these elements differ. Alternative implementations of amplifier 125 need not include step-down converter 210 and/or output energy storage device 230. Step-up converter 220 (or another type of amplifier in alternative embodiments) is required, however, as it is the purpose of switch-mode amplifier 125 to selectively amplify charge voltage 122. In many embodiments, one or both of step-up converter 220 or step-down converter 210 includes an output energy storage device such as device 230. Thus, with respect to references hereafter to step-up converter 220 or step-down converter 210, it will be understood that they may include one or more output energy storage devices, which may be a shared device. For clarity and for illustrative purposes, separate references are also made hereafter to output energy storage device 230.

As shown in FIG. 2, device 120 provides charge voltage 122 to step-down converter 210A. Step-down converter 210A selectively decreases charge voltage 122 to generate step-down voltage 212A. This selective decreasing is accomplished in response to a control signal from controller 115 transmitted over control-signal line 202. Step-up converter 220A receives step-down voltage 212A and selectively amplifies it to generate amplified voltage 222A. This selective amplification is accomplished in response to a control signal from controller 115 over control-signal line 204. Output energy storage device 230A receives amplified voltage 222A and filters it to provide output voltage 232A, which is provided to biphasic converter 130.

The functions shown in FIG. 3 with respect to switch-mode amplifier 125B are the same as those just described with respect to amplifier 125A, except that the step-up converter precedes the step-down converter, rather than following it. Thus, with reference to FIG. 3, it is shown that device 120 provides charge voltage 122 to step-up converter 220B. Step-up converter 220B selectively amplifies charge voltage 122 to generate amplified voltage 222B in response to a control signal from controller 115. Step-down converter 210B receives amplified voltage 222B and selectively decreases it to generate step-down voltage 212B in response to a control signal from controller 115. Output energy storage device 230B receives step-down voltage 212B and filters it to provide output voltage 232B, which is provided to biphasic converter 130.

Figure 4:
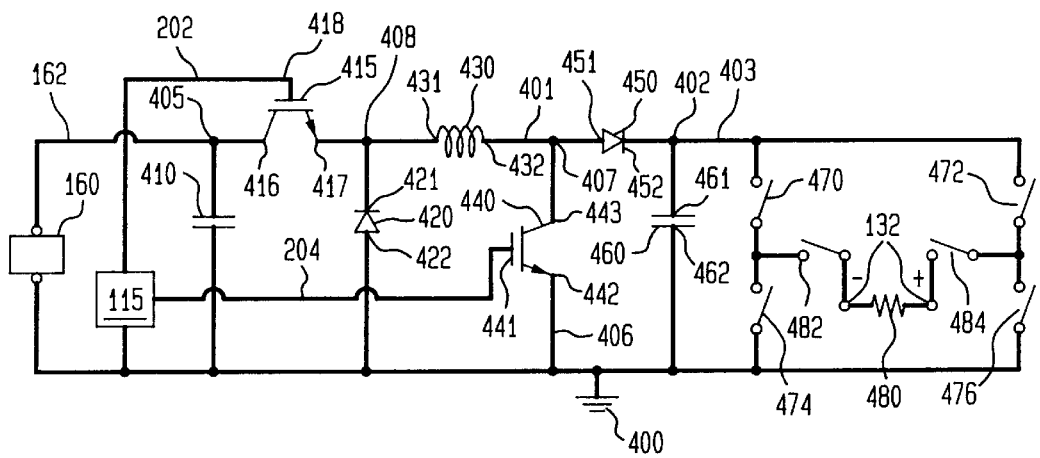
FIG. 4 is a simplified circuit diagram of one implementation of the switch-mode amplifier of FIG. 2, including a biphasic converter.

The operations of switch-mode amplifier 125A of FIG. 2 are now more fully explained with reference to the simplified circuit diagram of FIG. 4 and the waveforms shown in FIG. 5. The correspondences between the functional elements of FIG. 2 and the circuit elements of FIG. 4 are as follows. Rapid-discharge energy storage device 120 of FIG. 2 is implemented in the circuit of FIG. 4 by capacitor 410. Output energy storage device 230A is implemented by output capacitor 460. Step-down converter 210A is implemented by buck transistor (hereafter, buck switch) 415, buck diode 420, inductor 430, and capacitor 460. Step-up converter 220A is implemented by boost transistor (hereafter, boost switch) 440, boost diode 450, inductor 430, and capacitor 460. Thus, inductor 430 and capacitor 460 are shared by step-down converter 210A and step-up converter 220A in this implementation, thereby advantageously reducing the number of components required to implement switch-mode amplifier 125A. Biphasic converter 130 is implemented by the H-bridge made up of switches 470, 472, 474, and 476. Load resistor 480 represents the impedance of the patient. It will be understood that this representation is a simplification for purposes of illustration, and that patient impedance may also include capacitive and/or inductive components or, more generally, complex resistive and reactive attributes. Patient isolation relay 140 is implemented by switches 482 and 484 (which may be any of a variety of electrical or mechanical switches). Initial impedance sensor 135 is omitted for clarity.

As shown in FIG. 4, defibrillation voltage generator 160 provides defibrillation voltage 162 to one side of capacitor 410 at source node 405. The other side of capacitor 410 is connected to a common voltage 400. For convenience, common voltage 400 is assumed to be ground, but it need not be so. Buck switch 415 has a first node 416 that is connected to source node 405, and a control node 418 that is connected to control-signal line 202 from controller 115. Buck switch 415 also has a second node that is connected to input node 431 of inductor 430, and is also connected to output node 421 of buck diode 420. Buck diode 420 has an input node 422 that is connected to common voltage 400. Inductor 430 has an output node 432 that is connected to a first node 443 of boost switch 440 and to input node 451 of boost diode 450. Boost switch 440 also has a second node 442 that is connected to common voltage 400 and a control node 441 that is connected to controller 115 via control-signal line 204. Boost diode 450 has an output node 452 that is connected to an first node 461 of capacitor 460 and to two legs of the H-bridge consisting of switches 470 and 472. Capacitor 460 has a common node 462 connected to common voltage 400. The other two legs of the H-bridge consists of switches 474 and 476. As is evident, when switches 470 and 476 on opposite legs of the H-bridge are closed, and switches 472 and 474 are open, and assuming that patient isolation relay switches 482 and 484 are closed, current flows through switch 470, load resistor 480, and switch 476 to common (i.e., to the node connected to common voltage 400). Under the same assumption, when switches 472 and 474 on opposite legs of the H-bridge are closed, and switches 470 and 476 are open, current flows through switch 472, load resistor 480, and switch 474 to common.

As noted, buck switch 415 or boost switch 440 may be implemented by insulated-gate bipolar transistors, field-effect transistors, or other known solid state devices or similar devices now developed or to be developed in the future. Buck diode 420 or boost diode 450 may be implemented by properly synchronized transistor switches. H-bridge switches 470, 472, 474, or 476 may similarly be implemented by insulated-gate bipolar transistors, field-effect transistors, silicon controlled rectifiers, or other known solid state devices or similar devices to be developed in the future. Any of these switches or diodes need not be limited to single components but may include, for example, series or parallel combinations of insulated-gate bipolar transistors, or diodes properly snubbed and controlled for sharing voltage and current. The design and use of such combinations are well known by those skilled in the relevant art.

Figure 5:
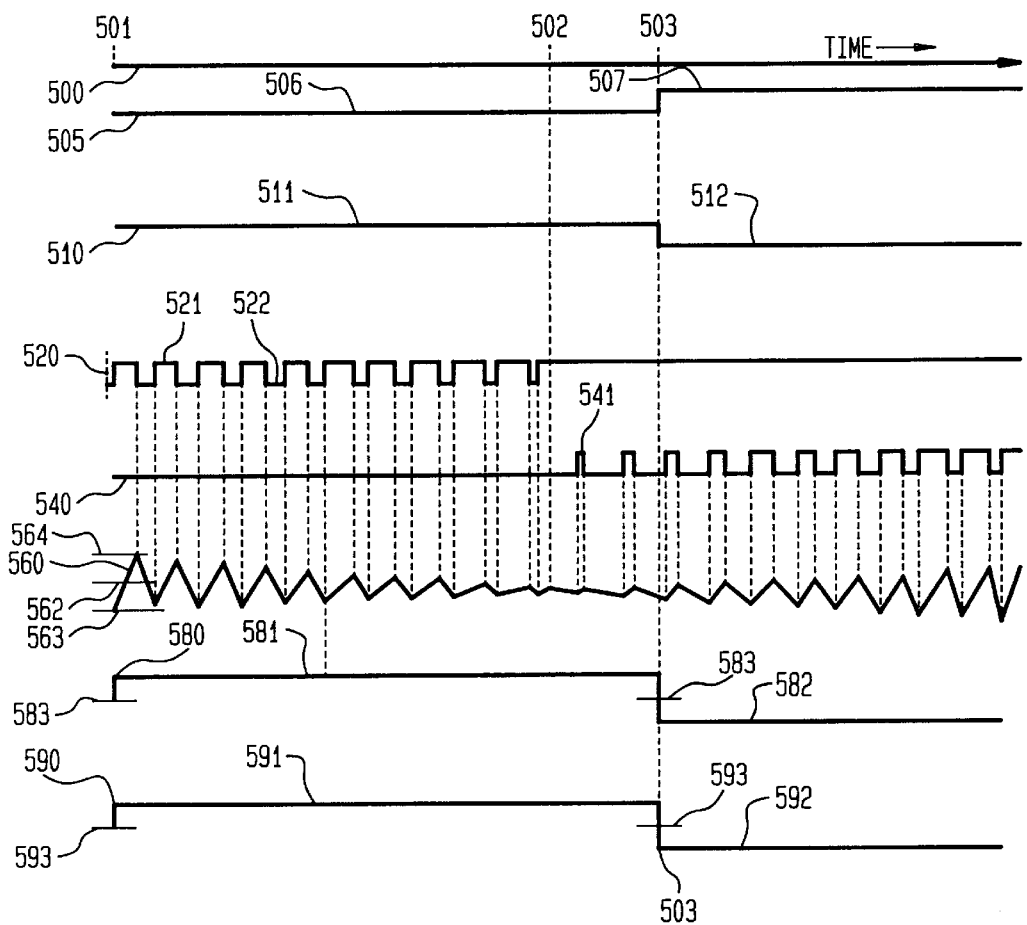
FIG. 5 is a graphical representation of illustrative embodiments of control signals to, and resulting current and voltage waveforms of, selected circuit elements of the circuit of FIG. 4, aligned along a common time axis.

FIG. 5 is a graphical representation of illustrative embodiments of control signals to, and resulting current and voltage waveforms of, selected circuit elements of the circuit of FIG. 4, aligned along a common time axis. This common time axis is represented by time line 500. It is illustratively assumed that, prior to initial time 501 shown on time line 500, operator 150 has activated activator 170 so that defibrillation voltage generator 160 has charged rapid-discharge energy storage device 120 to produce charge voltage 122. It is also illustratively assumed that, prior to initial time 501 and again in response to the activation of activator 170 by operator 150, activator 170 has enabled initial impedance sensor 135.

Control signal 505 controls the states of H-bridge switches 470 and 476. In the illustrative example, control signal 505 is a voltage waveform indicating that, from initial time 501 to a subsequent time 503, a control voltage applied to switches 470 and 476 is in a low state that is arbitrarily assumed for illustrative purposes to indicate that these switches are open. For example, voltage level 506 may be zero volts. At time 503, the voltage level of control signal 505 increases to a positive voltage 507; e.g., five volts. This high voltage state is assumed to indicate that switches 470 and 476 are closed. It will be understood that these voltage levels are arbitrarily chosen in this example, that signals consisting of other than bi-level voltages may be used, and that, more generally, a wide variety of control signals could be used to open and close the switches. In one illustrative implementation consistent with the chronaxie time of the human heart, time 503 may be approximately six milliseconds. As will be evident to those skilled in the relevant art, biphasic conversion is accomplished by switching H-bridge switches 472 and 474 off at approximately the same time switches 470 and 476 are switched on. Thus, in the illustrative implementation, control signal 510 indicates that the switches 472 and 474 are initially closed, as indicated by the initial high voltage 511 (e.g., five volts). At time 503, these switches are opened, as indicated by low voltage 512.

Control signals 505 and 510 are generated in the illustrated embodiment by controller 115. Any of a variety of known timing circuits, devices, or techniques may be used to generate these signals. Also, in alternative embodiments, the biphasic control signals for the H-bridge or other biphasic converter need not be generated by controller 115.

Rather, they may be provided by timing circuits or devices included in biphasic converter 130 or another element of defibrillator 105. Further, control signals 505 and 510 need not be based on a timing element, but may be triggered by other events such as a voltage at any of the elements of amplifier 125A reaching or crossing predetermined levels.

A flow of current through switches 472 and 474 during the time period between time 501 and time 503 generates what will arbitrarily be termed a "positive" voltage across load resistor 480, as indicated in FIG. 4. Thus, biphasic output voltage 132 (the voltage that is applied through the paddles to the patient) has a positive phase during this time period. As is evident, biphasic output voltage 132 has a negative phase subsequent to time 503 because current flows in the opposite direction through load resistor 480.

Buck control signal 520 of the illustrated embodiment is a voltage applied to control node 418 of buck switch 415 by controller 115 over control-signal line 202. In the illustrated embodiment, buck switch 415 (like boost switch 440) acts as a switch. It is illustratively assumed that when control signal 520 is in a high state, such as voltage 521 of FIG. 5 (for example, five volts), buck switch 415 is closed. When buck control signal 520 is in a low state, such as voltage 522, buck switch 415 is open. The resulting pulse-width modulation represented by buck control signal 520 (and boost control signal 540 discussed below) are shown in FIG. 4 as being of fixed frequency. However, as will be evident to those skilled in the relevant art, alternative techniques may be used, such as constant on or off time and variable frequency modulation, or hysteretic control.

The time period between initial time 501 and subsequent time 502, as shown on time line 500 of FIG. 5, is a period in which buck switch 415 is intermittently open and closed in accordance with the pulses of buck control signal 520. However, as indicated by the portion of boost control signal 540 from time 501 to time 502, boost switch 440 is constantly open. Thus, this time period may be referred to as the "buck phase." The duration of the buck phase in this illustrative example arbitrarily is assumed to be approximately 4.8 milliseconds. During each on-pulse of buck control signal 520, a current flows through inductor 430 to output capacitor 460, as will be evident to those skilled in the relevant art. That current is represented in FIG. 5 as inductor current waveform 560. In this illustrative example, inductor current waveform 560 varies from a low represented by current level 563, to a high represented by current level 564. An intermediate current level 562 also is shown. Typical values for these current levels in the illustrated embodiment may be 18 amps for current level 563, 20 amps for current level 562, and 22 amps for current level 564. For clarity, these current levels are not drawn across the entire length of the time axis, but are merely suggested at the beginning of the axis. As is evident, the current through inductor 430 increases while buck switch 415 is closed and decreases while buck switch 415 is open and diode 420 is conducting, producing a triangular waveform.

Advantageously, controller 115 adjusts the widths of the pulses of control signal 520 (or other parameters in alternative implementations of pulse-width or frequency modulation or hysteretic control) to control the current flowing through inductor 430, switch 472, load resistor 480, and switch 474 to common. As is evident, output capacitor 460 provides filtering of the high frequency pulsatile output. With respect to the time periods noted for control signal 520, for example, and for a typical representational patient resistance of approximately 50 ohms, output capacitor 460 may be a film capacitor with a capacitance of approximately one-half to five microfarads, for example.

In one mode of operation, output capacitor 460 also advantageously minimizes leakage current applied to the patient circuit (the circuit through switches 482 and 484, and load resistor 480) just prior to firing of the defibrillator. In this mode, output capacitor 460 does not charge at the same time as rapid-discharge energy storage device 120 charges. Rather, output capacitor 460 charges when the defibrillator is fired. Thus, leakage from buck transistor 415 typically would not have sufficient time to accumulate a dangerous charge on output capacitor 460; i.e., a charge of sufficient magnitude to cause an arc over the patient isolation relays, or that would present a danger to a patient or operator if the relays erroneously closed.

As noted, controller 115 selectively turns buck switch 415 off and on based in part on the indicator of patient impedance, which may be measured by measuring current flow (or voltage levels) at various places in amplifier 125A. For example, a current sensor could be positioned at circuit branch 406 as shown in FIG. 4 to measure the current flowing through boost switch 440. Similarly, a current sensor could be positioned at locations such as point 401 (to measure current flowing through inductor 430), point 403 (to measure the output current), at any switch or diode branch, or at any other circuit branch. Appropriate locations at which to place current, and/or voltage, sensors will be evident to those skilled in the relevant art. Feedback sensor 145 of FIGS. 1–3 represents this function of sensing the indicator of patient impedance and providing a measure of it to controller 115. Connecting line 224 of FIG. 2 represents an implementation in which a sensor is positioned in step-up converter 220A (such as at circuit branch 406). Connecting line 214 represents an alternative implementation in which a sensor is positioned in step-down converter 210A, and connecting line 216 represents yet another implementation in which a sensor is positioned between output energy storage device 230 and biphasic converter 130 (such as at point 403). Lines 224, 214, and 216 are shown as dotted lines to indicate that, in alternative implementations, any one, or any combination, of them may be employed. Similarly, alternative feedback paths are indicated with respect to the configuration of FIG. 3 by lines 324, 314, and 316.

As may be noted from FIG. 5, the amplitudes of successive saw teeth of inductor current waveform 560 decline during the buck phase as rapid-discharge energy storage device 120 discharges. Charge voltage 122 thus declines and approaches output voltage 232A. During this period, the voltage across load resistor 480 is approximately constant due to the choice of the frequency of control signal 520 as compared to the time constant for the LRC circuit represented by output capacitor 460 (e.g., 1 to 5 microfarads), inductor 430, and load resistor 480 (a patient-dependent value that may be, for example, 50 ohms). As is known to those skilled in the relevant art, the average voltage at node 407 is equal to the duty cycle of buck switch 415 times a time-averaged value of the charge voltage 122 (which declines over time). The duty cycle is the ratio of the time that buck switch 415 is closed to the period of constant-frequency pulse-width modulated signal 520.

Thus, by varying the duty cycle during the buck phase (specifically, by increasing it as charge voltage 122 decreases), the voltage at node 402 may be maintained at an approximately constant level, such as voltage 581. In a typical defibrillator application, voltage 581 may be approximately 1,000 volts, for example. In output voltage waveform 580, voltage 581 is shown in relation to a reference voltage 583 that, in this illustrative example, is assumed to be zero volts. Because of the step-down conversion, voltage 581 may advantageously be less than the initial value of charge voltage 122. Also advantageously, step-down conversion prior to step-up conversion reduces the range of duty cycle over which either conversion stage must operate. Thus, circuit component stresses are reduced and efficiency is increased. Techniques for optimization of these effects will be evident to those skilled in the relevant art.

As charge voltage 122 declines, the amplitudes of the teeth of inductor current waveform 560 successively decline until input voltage 122 and output voltage 232A are equal. Controller 115 then initiates a "boost phase," meaning that boost switch 440 has a non-zero duty cycle. At the same time, buck switch 415 remains fully on. In the illustrative example of FIG. 5, this transition from buck phase to boost phase occurs at time 502, as shown on time line 500. During the boost phase, controller 115 increases the duty cycle of boost switch 440 from zero to increasingly larger values. Specifically, with reference to boost control signal 540 of FIG. 5, boost switch 440 is intermittently turned on beginning, in the illustrative example, with positive pulse 541. As may be noted with reference to buck control signal 520, buck switch 415 is turned on during the boost phase. Thus, only one converter is operational at a time, although it need not be so in alternative implementations.

During the boost phase, the boost circuit operation provides a higher voltage at node 402 than is present at node 408 (corresponding to the input to step-up converter 220A). This amplification occurs because energy is stored in inductor 430 when boost switch 440 is closed; i.e., boost switch 440 provides a current path to ground so that a current flows through inductor 430. When boost switch 440 is open, the inductive current is forced to flow through boost diode 450, into output capacitor 460, and thence through the H-bridge and load resistor 480. During this time when boost switch 440 is open, the induced voltage across inductor 430 is more positive at node 432, as measured with respect to node 431. Inductor 430 thus increases the voltage at node 402 beyond the voltage level at node 408 as it maintains current flow. During the boost phase, the voltage across load resistor 480 is proportional to charge voltage 122 times the ratio of one divided by one minus the duty cycle. Thus, controller 115 may selectively maintain, or increase, the voltage across load resistor 480 by altering the duty cycle applied via control-signal lines 202 and 204 to buck switch 415 and boost switch 440, respectively. By cascading the H-bridge to the combination of buck and boost stages, the phase of the voltage across load resistor 480 may be varied. Such a phase switch is shown in FIG. 5 at time 503, resulting in a switch of the voltage across load resistor 480 from a positive level of 581 to an equal in magnitude, but negative, level of 582.

Waveform 590 of FIG. 5 illustrates the current through load resistor 480. As is evident, the shape of current waveform 590 will be the same as that of voltage waveform 580 because load resistor 480 is illustratively assumed to be a pure resistor. In practice, waveforms 580 and 590 may slightly differ because this illustrative assumption may not be precisely accurate. Assuming a resistance of 50 ohms for load resistor 480, and the voltages across it referred to above, current waveform 590 is maintained at a positive level 591 (20 amps) with respect to reference level 593 (0 amps) until time 503. At time 503 the phase shift occurs, and the current through load resistor 480 is shown by level 592 (negative 20 amps).

Figure 6:
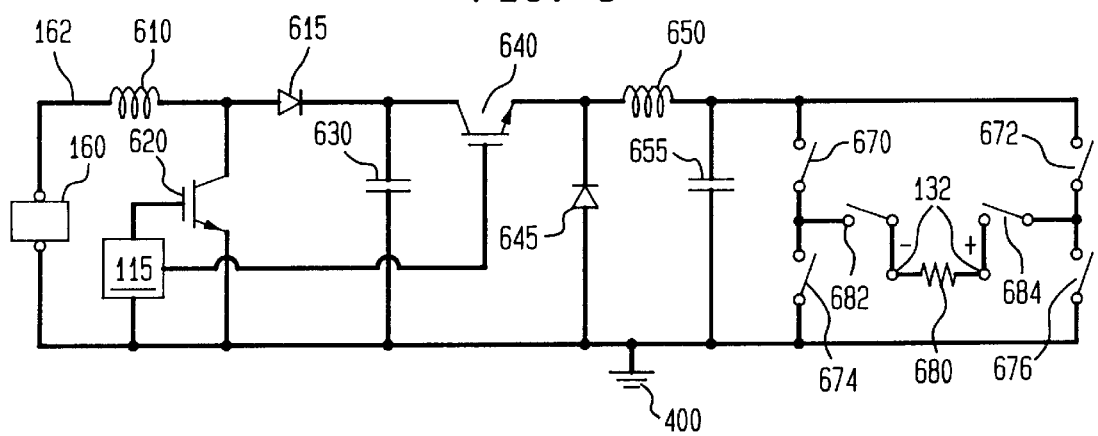
FIG. 6 is a simplified circuit diagram of one implementation of the switch-mode amplifier of FIG. 3.

From the preceding explanation of the operation of amplifier 125A, the operation of switch-mode amplifier 125B (a simplified circuit diagram of which is provided in FIG. 6) will be evident to one skilled in the relevant art. As shown in FIG. 6, amplifier 125B includes a step-up converter made up of inductor 610, boost switch (transistor) 620, boost diode 615, and capacitor 630. The connections among these components of the step-up converter are the same as the connections among the corresponding components of the step-up converter of FIG. 4. However, whereas the inductor of the step-up converter had been shared with the inductor of the step-down converter in the configuration described above with respect to FIG. 4, separate inductors (610 and 650) are used in the implementation of FIG. 6. Similarly, whereas in the configuration of FIG. 4 output capacitor 460 is shared, separate capacitors 630 (for the step-up converter) and 655 (for the step-down converter) are employed in the embodiment of FIG. 6. Amplifier 125B also includes a step-down converter made up of buck switch (transistor) 640, diode 645, inductor 650, and output capacitor 655. The connections among these components of the step-down converter generally are the same as the connections among the corresponding components of the step-down converter of FIG. 4. Output capacitor 655 may be omitted in alternative embodiments. Advantageously, as previously noted, inductor 650 provides a good constant-current source. As in the case of amplifier 125A, an H-bridge, consisting of switches 670, 672, 674, and 676, is also provided for biphasic conversion. Patient isolation relay 140 is implemented by switches 682 and 684.

As will also be evident to those skilled in the relevant art, a number of other circuit designs and topologies may be used to implement switch-mode amplifier 125. Some alternative topologies include a step-up converter but not a step-down converter. Some include both and employ a single switch for both functions. Some incorporate the biphasic conversion function within one or both of the step-up or step-down converters. More generally, biphasic output waveforms may be produced either by employing step-up and step-down converters in a push-pull amplifier type configuration, or a single converter may be followed by an H bridge or similar circuit. An illustrative group of such alternative topologies are now described with respect to FIGS. 7 through 12. It will be understood, however, that these topologies are illustrative and not limiting, and that many variations of the illustrated embodiments of FIGS. 7 through 12 are also possible within the scope of the present invention.

It will also be understood that these illustrative circuits are simplified to depict the principal topology only. They may omit elements or connections where such omissions will be apparent to those skilled in the relevant art. For example, control signals to transistor switches are not shown; rather, for clarity, a simple switch symbol is used to represent transistor switch elements.

Figure 7:
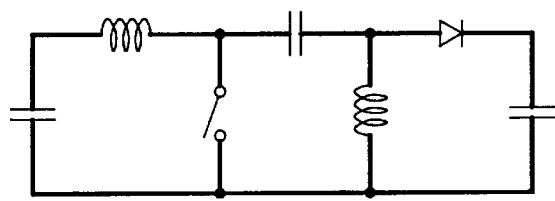
FIG. 7 is a simplified circuit diagram of one embodiment of an alternative sepic-type implementation of a switch-mode amplifier of FIG. 1.
Figure 8:
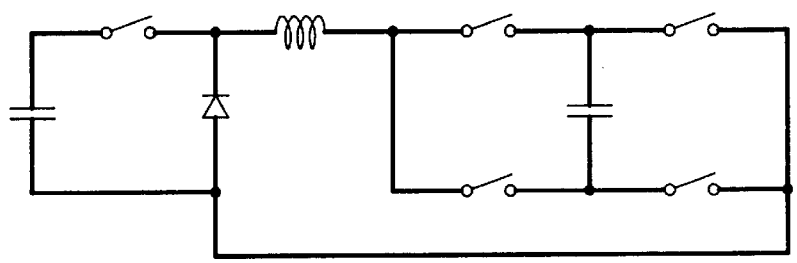
FIG. 8 is a simplified circuit diagram of one embodiment of an alternative buck-followed-by-boost-bridge-type implementation of a switch-mode amplifier of FIG. 1.
Figure 9:
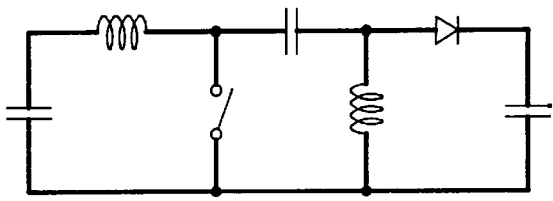
FIG. 9 is a simplified circuit diagram of one embodiment of an alternative cuk'-type implementation of a switch-mode amplifier of FIG. 1.
Figure 10:
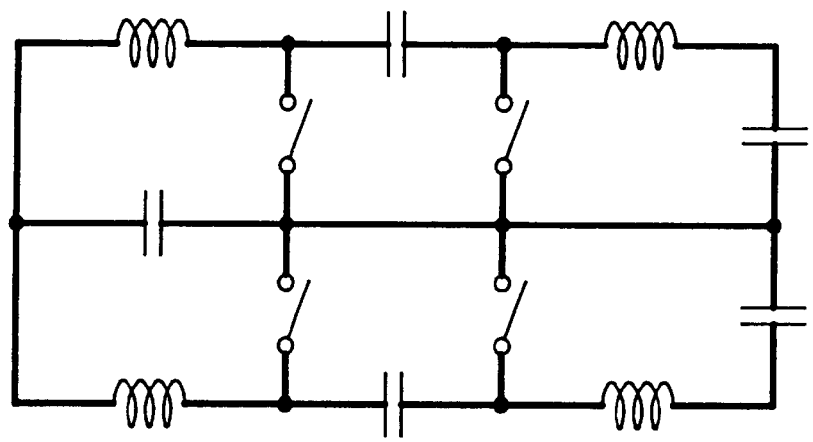
FIG. 10 is a simplified circuit diagram of one embodiment of an alternative push-pull cuk'-type implementation of a switch-mode amplifier of FIG. 1.
Figure 11:
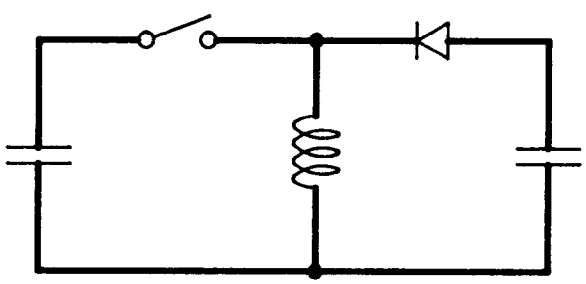
FIG. 11 is a simplified circuit diagram of one embodiment of an alternative simple-fly-back-type implementation of a switch-mode amplifier of FIG. 1.
Figure 12:
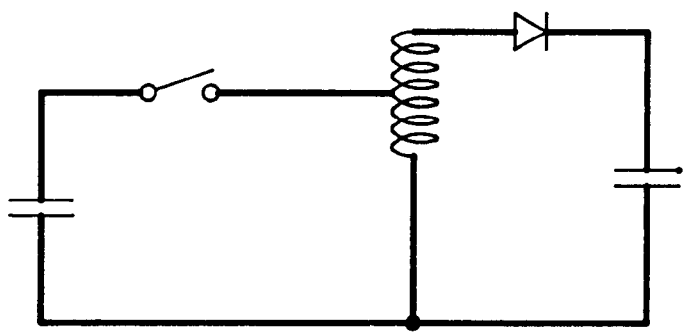
FIG. 12 is a simplified circuit diagram of one embodiment of an alternative simple-boost, tapped-inductor-type implementation of a switch-mode amplifier of FIG. 1.

FIG. 7 is a simplified circuit diagram of one embodiment of a conventional sepic-type implementation of switch-mode amplifier 125 of FIG. 1. This circuit includes both step-up and step-down conversion using a single switch, and is non-inverting. FIG. 8 is a simplified circuit diagram of one embodiment of a conventional buck-followed-by-boost-bridge-type implementation of switch-mode amplifier 125 of FIG. 1. This circuit advantageously combines the H-bridge with the boost switch and boost diode functions. FIG. 9 is a simplified circuit diagram of one embodiment of a conventional cuk'-type implementation of switch-mode amplifier 125 of FIG. 1. This circuit accomplishes a buck-boost conversion with a single switch and has an inverted polarity output. Note that with this topology, as well as the sepic topology and many others with dual inductors, the inductors may advantageously share a common structure (mutual inductance) with leakage inductance advantageously placed to reflect ripple current. An additional winding may also be added to the inductors of any of these converters to reflect the ripple current into an added capacitor that is not part of the output. FIG. 10 is a simplified circuit diagram of one embodiment of a conventional push-pull cuk'-type implementation of switch-mode amplifier 125 of FIG. 1. This circuit modifies that of FIG. 9 so that a push-pull feature is implemented. More generally, as will be evident to those skilled in the relevant art, FIG. 9 is illustrative of how any of the topologies of FIGS. 4–7, 11, 12, and others, may be modified to a push-pull configuration. The push-pull modification provides for phase inversion without the addition of an H-bridge. FIG. 11 is a simplified circuit diagram of one embodiment of a conventional simple-fly-back-type implementation of switch-mode amplifier 125 of FIG. 1. This circuit accomplishes a buck-boost function with an inverted polarity. FIG. 12 is a simplified circuit diagram of one embodiment of a conventional simple-boost, tapped-inductor-type implementation of switch-mode amplifier 125 of FIG. 1. This circuit accomplishes the standard boost function with an increase in output voltage beyond the standard boost. The switch sees lower voltage stress, but higher current stress, compared to the standard converter.

Controller 115 and Waveform Definer 110

As noted, defibrillation waveform generator 100 includes controller 115 and also optionally includes waveform definer 110. Waveform definer 110 provides to controller 115 the reference parameters of a selected waveform. These reference parameters may be provided to waveform definer 110 in accordance with any of a variety of known techniques. For example, parameters corresponding to a set of alternative waveforms may be stored in a data structure, such as is represented by waveform template 112 shown in FIG. 1. This data structure may be implemented in hardware, software, firmware, circuits of electronic components designed to store data, or in accordance with any of a variety of other known techniques.

Operator 150 selects a waveform in accordance with any of a variety of factors. For example, operator 150 (either a human being or a machine) may select a bi-phasic rectilinear waveform of particular amplitudes and durations based on the condition of the patient or other factors. Under other conditions, operator 150 may select different amplitudes or durations, or may select a sinusoidal waveform, and so on.

Controller 115 compares the waveform-reference parameters of the selected waveform to indicators or system performance (referred to as "system-performance parameters") provided by feedback sensor(s) 145 (or, initially, by initial impedance sensor 135). For example, controller 115 may compare a desired amplitude of biphasic output voltage 132 to an indicator of actual biphasic output voltage 132 provided by feedback sensor 145. There may be a difference between these amplitudes; i.e., there may be a difference between a waveform-reference parameter and a corresponding system-performance parameter. This difference is referred to for convenience as an error value. If there is an error value, controller 115 brings the actual value into conformance with the desired value by changing one or both of the control signals to the step-up or step-down converters of amplifier 125. It may be required that the error value exceed a threshold value before corrective action is taken. Controller 115 thus monitors the error value, and takes corrective action, until the error value is reduced to an acceptable level.

For example, it may be desirable to provide to the patient a positive pulse of constant current followed by a negative pulse of constant current. The parameters provided by waveform definer 110 to controller 115 typically would thus include the duration and phases of both pulses, the time that should elapse between them, and their amplitudes. Controller 115 provides control signals to switch-mode amplifier 125 and biphasic converter 130 to generate a current waveform having these desired parameters. As noted, various known modulation techniques may be employed for this purpose. Feedback sensor 145 provides controller 115 with system-performance parameters, such as, for example, an indicator of instantaneous current being delivered to the patient. If this current is less than the desired current as specified by one or more reference parameter, controller 115 modifies the control signal to the step-up converter of switch-mode amplifier 125 so that the current delivered to the patient is increased. Further details of the implementation of such an error-driven control loop to modify control signals to a switch-mode amplifier will be evident to those skilled in the relevant art. It will be understood that the reference parameters and system-performance parameters may be measures of voltage, current, charge, energy, other parameters, or combinations thereof. Also, these parameters may be instantaneous, average, peak, or another measure. In alternative embodiments, a feedback signal may be omitted. Rather, controller 115 may modulate the switches so as to obtain a particular output assuming the patient impedance to be unchanging.

In some implementations, waveform definer 110 may be limited to providing only reference parameters establishing amplitude and/or duration rather than also providing reference parameters that establish the form of the waveform (e.g., rectilinear, sinusoidal, etc.). For example, it may be determined that a bi-phasic rectilinear waveform is generally superior to any other form. Also, the functions of waveform definer 110 may be included in the functions of controller 115, particularly if a variety of forms of waveforms are not required.

Having now described one embodiment of the present invention, it should be apparent to those skilled in the relevant art that the foregoing is illustrative only and not limiting, having been presented by way of example only. For instance, many other schemes for distributing functions among the various functional elements of the illustrated embodiment are possible in accordance with the present invention. The functions of any element may be carried out in various ways in alternative embodiments. Thus, numerous variations are contemplated in accordance with the present invention to generate control signals, detect events or timing information to initiate or end control signals, provide or respond to feedback signals, and so on. Similarly, control signals may be voltage and/or current signals employing any of a variety of known, or to-be-developed, techniques including, but not limited to, pulse-width, frequency, or hysteretic modulation.

There are many possible variations of circuit topologies and circuit elements that may carry out the functions described herein with respect to the present invention. For example, a variety of known, or to-be-developed, step-up converters, step-down converters, biphasic converters, rapid-discharge energy storage devices, switch-mode amplifiers, and feedback sensors, may be used. The functions of controller 115 similarly may be implemented in accordance with a wide variety of known techniques. For example, they may be implemented by discrete or integrated electronic components, or controller 115 may be a microprocessor. Moreover, the functions described above with respect to controller 115 need not be performed by only one, or a single collection of, circuit or devices. Rather, the functions may be distributed among various other functional elements of the invention. For example, control over biphasic converter 130 may be accomplished by a circuit integral with converter 130 rather than provided over a control-signal line from controller 115. Various known limiting techniques may be applied to the step-up or step-down converters to prevent over-voltage or over-current at the output, as might occur, for example, for open or shorted paddles. Dissipation of stored energy may occur in a separate dump resistor, or in the inductor if properly controlled. Numerous other embodiments, and modifications thereof, are contemplated as falling within the scope of the present invention as defined by appended claims and equivalents thereto.

What is claimed is:

1. A defibrillation waveform generator for generating a defibrillator waveform using a defibrillation voltage from a voltage generator, the defibrillation waveform generator comprising:
   a rapid-discharge energy storage device charged by the voltage generator so as to store a charge voltage, the rapid-discharge energy storage device tuned consistently with a chronaxie time of a human heart;
   a controller constructed and arranged to generate at least one control signal; and
   an amplifier, responsive to one or more of the control signals, constructed and arranged to selectively amplify the charge voltage so as to enable generation of a variable defibrillation waveform.

2. The defibrillation waveform generator of claim 1, wherein:
   the amplifier is a switch-mode amplifier.

3. The defibrillation waveform generator of claim 2, wherein:
   the amplifier comprises
      a step-up converter having at least one boost switch responsive to a first control signal, constructed and arranged to selectively amplify the charge voltage to generate an amplified voltage.

4. The defibrillation waveform generator of claim 3, further comprising:
   a feedback sensor, constructed and arranged to provide at least one system-performance parameter to the controller; and
   wherein the controller is further constructed and arranged to determine at least one waveform-reference parameter;
      compare the system-performance parameter to the waveform-reference parameter to determine at least one error value; and
      modify the first control signal to reduce the error value.

5. The defibrillation waveform generator of claim 3, wherein:
   the amplifier further comprises
      a step-down converter having at least one buck switch responsive to a second control signal, constructed and arranged to selectively decrease the charge voltage.

6. The defibrillation waveform generator of claim 5, wherein:
   the at least one boost switch and the at least one buck switch are the same switch.

7. The defibrillation waveform generator of claim 5, further comprising:
   a feedback sensor, constructed and arranged to provide at least one system-performance parameter to the controller; and
   wherein the controller is further constructed and arranged to
      determine at least one waveform-reference parameter;
      compare the system-performance parameter to the waveform-reference parameter to determine at least one error value;
      modify the first control signal to reduce the error value; and
      modify the second control signal to reduce the error value.

8. The defibrillation waveform generator of claim 3, wherein:
   the amplifier further comprises
      a step-down converter having at least one buck switch responsive to a second control signal, constructed and arranged to selectively decrease the amplified voltage.

9. The defibrillation waveform generator of claim 3, further comprising:
   a biphasic converter constructed and arranged to biphasically convert the amplified voltage to provide a biphasic output voltage.

10. The defibrillation waveform generator of claim 9, wherein:
    the biphasic converter is an H-bridge.

11. The defibrillation waveform generator of claim 9, wherein:
    the biphasic converter is a push-pull amplifier.

12. The defibrillation waveform generator of claim 10, wherein:
    the step-up converter and the H-bridge share at least one switch.

13. The defibrillation waveform generator of claim 3, further comprising:
    a waveform definer constructed and arranged to provide to the controller at least one reference parameter of at least one defibrillation waveform.

14. The defibrillation waveform generator of claim 13, further comprising:
    an initial impedance sensor constructed and arranged to provide to the waveform definer an indicator of an initial patient impedance.

15. The defibrillation waveform generator of claim 3, further comprising:
    an initial impedance sensor constructed and arranged to provide to the controller an indicator of an initial patient impedance.

16. The defibrillation waveform generator of claim 2, wherein:
    the amplifier comprises
       a step-down converter, constructed and arranged to selectively decrease the charge voltage to generate a step-down voltage, having at least one buck switch responsive to a second control signal, and
       a step-up converter, constructed and arranged to selectively amplify the step-down voltage to generate an amplified voltage, having at least one boost switch responsive to a first control signal.

17. The defibrillation waveform generator of claim 16, wherein:
    the step-down converter and the step-up converter share an inductor.

18. The defibrillation waveform generator of claim 16, wherein:

the step-down converter and the step-up converter share a capacitor.

19. The defibrillation waveform generator of claim 16, further comprising:

a feedback sensor, constructed and arranged to sense an indicator of patient impedance provided by the step-up converter, electrically coupled to the controller.

20. The defibrillation waveform generator of claim 16, further comprising:

a feedback sensor, constructed and arranged to sense an indicator of patient impedance provided by the step-down converter, electrically coupled to the controller.

21. A defibrillator, comprising:

a power supply, a defibrillation voltage generator electrically coupled to the power supply, constructed and arranged to generate a defibrillation voltage; and a defibrillation waveform generator for generating a defibrillator waveform, the defibrillation waveform generator including:

a rapid-discharge energy storage device having a charge voltage, electrically coupled to the defibrillation voltage generator;

a controller constructed and arranged to generate at least one control signal; and an amplifier, responsive to one or more of the control signals, constructed and arranged to selectively amplify the charge voltage so as to enable generation of a variable defibrillation waveform.

22. The defibrillator of claim 21, wherein:

the amplifier is a switch-mode amplifier.

23. The defibrillator of claim 22, wherein:

the amplifier comprises a step-up converter having at least one boost switch responsive to a first control signal, constructed and arranged to selectively amplify the charge voltage to generate an amplified voltage.

24. The defibrillator of claim 22, wherein:

the amplifier comprises a step-down converter, constructed and arranged to selectively decrease the charge voltage to generate a step-down voltage, having at least one buck switch responsive to a second control signal, and a step-up converter, constructed and arranged to selectively amplify the step-down voltage to generate an amplified voltage, having at least one boost switch responsive to a first control signal.

25. The defibrillator of claim 21, wherein:

the defibrillation waveform generator is externally coupleable to a human being.

26. The defibrillator of claim 21, wherein:

the defibrillation waveform generator is implantable within a human being.

27. A method for generating a defibrillator waveform, comprising:

charging a rapid-discharge energy storage device to a charge voltage, wherein the storage device is tuned consistently with a chronaxie time of a human heart;

generating at least one control signal; and selectively amplifying the charge voltage responsive to one or more of the control signals so as to enable generation of a variable defibrillation waveform.

28. The method of claim 27, wherein:

the generating step comprises:

generating a pulse-width modulated control signal.

29. The method of claim 27, wherein:

the generating step comprises:

generating a pulse-frequency modulated control signal.

30. The method of claim 27, wherein:

the selectively amplifying step comprises:

switch-mode amplifying.

31. The method of claim 27, wherein:

the selectively amplifying step comprises step-up converting for selectively maintaining the charge voltage.

32. The method of claim 31, further wherein:

the selectively amplifying step comprises step-down converting for selectively decreasing the charge voltage, wherein the step up converting is responsive to a first control signal and the step-down converting is responsive to a second control signal.

* * * * *